United States Patent [19]

Bolis et al.

[11] Patent Number: 4,851,563

[45] Date of Patent: Jul. 25, 1989

[54] METHOD FOR THE REMOVAL OF THE FORMYL GROUP FROM AN ESTER OF AN N-FORMYL PEPTIDE OR N-FORMYL AMINOACID

[75] Inventors: Goffredo A. Bolis, Milan; Giuseppe Cantarini, Melegnano; Marco Da Col, Bologna, all of Italy

[73] Assignee: Lark S.p.A., Milan, Italy

[21] Appl. No.: 905,476

[22] Filed: Sep. 9, 1986

[30] Foreign Application Priority Data

Sep. 30, 1985 [IT] Italy ................................ 22310 A/85

[51] Int. Cl.$^4$ ........................................... C07C 101/02
[52] U.S. Cl. ....................................... 560/41; 530/801
[58] Field of Search .................... 560/38, 41; 530/801; 426/548

[56] References Cited

U.S. PATENT DOCUMENTS

| | | | |
|---|---|---|---|
| 4,021,418 | 5/1977 | Takemoto et al. | 560/38 |
| 4,071,511 | 1/1978 | Takemoto et al. | 560/171 |

FOREIGN PATENT DOCUMENTS

| | | | |
|---|---|---|---|
| 0169937 | 2/1986 | European Pat. Off. | 560/41 |
| 2098220 | 11/1982 | United Kingdom | 560/38 |

OTHER PUBLICATIONS

Geiger et al., *Chem. Ber.*, vol. 101, pp. 3386–3391 (1968).

*Primary Examiner*—Bruce D. Gray
*Attorney, Agent, or Firm*—Hedman, Gibson, Costigan & Hoare

[57] ABSTRACT

A method for the removal of the formyl group from an ester of an N-formyl peptide or N-formyl aminoacid, in which the ester is reacted with urea in the presence of a polar solvent and a strong acid.

7 Claims, No Drawings

METHOD FOR THE REMOVAL OF THE FORMYL GROUP FROM AN ESTER OF AN N-FORMYL PEPTIDE OR N-FORMYL AMINOACID

The present invention relates to a method for the removal of the formyl group from an ester of an N-formyl peptide or N-formyl aminoacid, particularly an ester of the aforesaid type having a free carboxyl group in the chain.

Methods of the aforesaid type for removing formyl groups lay particular importance on the production of the methyl ester of alpha-L-aspartyl-L-phenylalanine (aspartame) which is obtained by a condensation reaction between the anhydride of N-formyl-L-aspartic acid with the methyl ester of L-phenylalanine.

From U.S. Pat. No. 4,071,511 a deformylation method is known in which the N-formyl ester is reacted with a strong acid in aqueous solution and in the presence of an organic solvent, particularly alcohols. This method suffers from the disadvantage of poor selectivity since secondary reactions may take place, particularly hydrolysis of the ester group.

U.K. Pat. no. 2,098,220 describes a deformylation method which uses hydrazine and derivatives of hydrazine which apparently result in greater selectivity and a greater deformylation yield, but however requires the pH to be controlled precisely within the range 1 to 3.5 during the reaction.

The object of the present invention is to provide a new deformylation method of the type specified above which is highly selective and gives a high reaction yield, and which can be carried out with the use of reagents which are widely available on the market and of low cost.

For this purpose, the subject of the present invention is a method for the removal of the formyl group from a compound constituted by an ester of an N-formyl peptide or an N-formyl aminoacid characterised in that it includes the step of reacting the compound with urea in the presence of a polar solvent and a strong acid.

The method of the invention does not require rigorous control of the pH during the reaction although it is preferable for the initial reaction pH to be equal to or less than 1.

The reaction is preferably carried out with the use of hydrochloric acid, preferably in a ratio of 3-4 moles per mole of formyl group. However other acids such as sulphuric acid, nitric acid and phosphoric acid could be used.

The polar solvent used in the reaction is preferably selected from the group consisting of monohydroxy alcohols having from 1 to 4 carbon atoms, acetone, acetonitrile and dimethylformamide, possibly in the presence of water.

It is preferable to carry out the reaction with a stoichiometric excess of urea, preferably with 3-5 moles per mole of formyl group.

The reaction temperature is not critical since it influences solely the reaction rate. Typically the reaction is carried out at a temperature in the region of from 30° C. up to the temperature of reflux of the reaction solution.

The reaction yield is kept at a value above 60% and analysis of the reaction products has shown the absence of appreciable quantities of undesirable by-products.

The method of the invention will now be described with reference to the following examples which relate to the deformylation of N-formyl aspartame.

EXAMPLE 1

16.5g of a mixture of alpha+beta formyl aspartame, containing 13.4g (41.6 mmoles) of alpha-formyl aspartame are dissolved in a mixture of:
65ml $CH_3CN$
20ml methyl alcohol
11ml 37% HCl
12.5ml glacial acetic acid
10ml dimethylformamide
13g urea (216 mmoles)

The clear, colourless, homogeneous solution obtained is agitated at 50° C. for 30 hours. A final check on the products is effected by high pressure liquid chromatography (HPLC) and shows the following composition:

alpha-aspartame (ASP): 8.83g (30 moles); alpha-formyl aspartame (FASP); 2.03g
Yield: 72-1%.

EXAMPLE 2

13.4g of alpha-formyl aspartame (41.6 moles) are dissolved atambient temperature in a mixture of:
100ml acetone
11ml 37% HCl
12.5ml glacial acetic acid
13g urea (216 mmoles)

The clear, colourless, homogeneous solution obtained is agitated at 50° C. for 55 hours and then for a further 64 hours at ambient temperature.

The final composition determined by HPLC is as follows:

alpha-ASP: 9.58g (32.6 mmoles); alpha-FASP: 1.97g
Yield: 78.3%.

EXAMPLE 3

16.5g of a mixture of alpha-beta-formyl aspartame, containing 13.6g (42 mmoles) of alpha-formyl aspartame, are dissolved in a mixture of:
65ml $CH_3CN$
20ml methyl alcohol
11ml 37% HCl
12.5ml glacial acetic acid
13g urea The intitial pH of the solution is 0.15.

The clear, homogeneous, colourless solution obtained is heated to 50° C. and agitated at this temperature for 30 hours. The final pH is 0.3.

The final composition determined by HPLC is as follows:

alpha-ASP: 8.43g (28.7 mmoles); alpha-FASP: 0.88g
Yield: 67.8%.

EXAMPLE 4

13.5g of alpha-formyl aspartame are dissolved in a mixture of:
65ml $CH_3CN$
20ml tert. butyl alcohol
11ml 37% HCl
12.5ml glacial acetic acid
13g of urea The clear, colourless solution obtained is heated at 65° C. for 24 hours.

The final composition by HPLC is as follows:
alpha-ASP: 8.15g (27.7 mmoles); alpha-FASP: 0.82g
Yield: 66.1%.

EXAMPLE 5

16.5g of a mixture of alpha- and beta-formyl aspartame, containing 13.6g of alpha-formyl aspartame are dissolved in a mixture of:
65ml CH$_3$CN
20ml H$_2$O
11ml 37% HCl
12.5ml glacial acetic acid
13g urea
The solution obtained is agitated at 50° C. for 12 hours and then kept for 64 hours at ambient temperature.
Final composition by HPLC: alpha-ASP: 8.48g (28.8 mmoles); alpha-FASP: 1.1g
Yield 62.3%.

EXAMPLE 6

13.6g of alpha-formyl aspartame (42.2 mmoles) are dissolved in a mixture of:
65ml CH$_3$CN
20ml H$_2$O
11ml 37% HCl
12.5ml of glacial acetic acid
13g urea
The clear, colourless solution obtained is heated to 65° C. and agitated for 8 hours.
Final composition by HPLC: alpha-ASP: 8.37g (28.5 mmoles); alpha-FASP: 0.62g
Yield: 61.5%.
It is evaporated under vacuum to oil, diluted to 200ml with H$_2$O. The final water rich composition by HPLC: alpha-ASP: 7.97g; alpha-FASP: 0.59g.

What is claimed is:

1. A method for removing the formyl group from N-formyl peptide esters or N-formyl amino acid esters comprising contacting said ester with urea in the presence of a polar solvent and a strong acid until a deformylated ester is obtained.

2. A method according to claim 1, wherein the solvent is selected from the group consisting of monohydroxy alcohols having from 1 to 4 carbon atoms, acetone, acetonitrile and dimethylformamide.

3. A method according to claim 1, wherein the strong acid is hydrochloric acid and glacial acetic acid, and the solution is acidified to an initial pH of less than 1.

4. A method according to claim 1, wherein the urea is present in a stoichiometric excess of 3–5 moles of urea per mole of N-formyl group.

5. A method according to claim 1, wherein the deformylation reaction is carried out at a temperature of between 30° C. and the reflux temperature of the reaction mixture.

6. A method according to claim 1, wherein the ester is N-formyl-L-aspartyl-L-phenylalanine methyl ester.

7. A method for the deformylation of the methyl ester of N-formyl-L-aspartyl-L-phenylalanine consisting essentially of contacting said methyl ester with a mixture of 3–5 moles, per mole of the methyl ester, of urea and 3–4 moles, per mole of the methyl ester, of a combination of hydrochloric acid and glacial acetic acid in a polar solvent, wherein the initial pH of the reaction mixture formed on contacting said methyl ester and said mixture is less than or equal to 1, said contacting being carried out at a temperature between 30° C. and the reflux temperature of said reaction mixture, until alpha-L-asparatyl-L-phenylalanine methyl ester is obtained.

* * * * *